United States Patent
Cran

(10) Patent No.: US 10,654,862 B2
(45) Date of Patent: *May 19, 2020

(54) METHODS FOR THE CHEMICAL SYNTHESIS OF PYRROLE-LINKED BIVALENT COMPOUNDS, AND COMPOSITIONS THEREOF

(71) Applicant: AVEKSHAN LLC, Tallahassee, FL (US)

(72) Inventor: John Cran, Alachua, FL (US)

(73) Assignee: AVEKSHAN, LLC., Alachua, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/265,286

(22) Filed: Feb. 1, 2019

(65) Prior Publication Data

US 2019/0161491 A1 May 30, 2019

Related U.S. Application Data

(63) Continuation of application No. 15/558,808, filed as application No. PCT/US2016/023107 on Mar. 18, 2016, now Pat. No. 10,253,034.

(60) Provisional application No. 62/134,758, filed on Mar. 18, 2015.

(51) Int. Cl.
| | |
|---|---|
| *C07D 491/22* | (2006.01) |
| *C07D 489/08* | (2006.01) |
| *C07D 489/00* | (2006.01) |
| *A61K 31/403* | (2006.01) |
| *A61K 31/407* | (2006.01) |
| *G01N 30/02* | (2006.01) |
| *G01R 33/46* | (2006.01) |

(52) U.S. Cl.
CPC .......... *C07D 489/00* (2013.01); *A61K 31/403* (2013.01); *A61K 31/407* (2013.01); *C07D 491/22* (2013.01); *G01N 2030/027* (2013.01); *G01R 33/46* (2013.01)

(58) Field of Classification Search
CPC .. C07D 491/22; C07D 489/08; C07D 209/58; A61K 31/485
USPC ........ 546/26, 45; 548/439; 514/279
See application file for complete search history.

(56) References Cited

U.S. PATENT DOCUMENTS

| 4,649,200 A | 3/1987 | Portoghese et al. |
|---|---|---|
| 10,253,034 B2 * | 4/2019 | Cran .................... C07D 491/22 |
| 2009/0149528 A1 | 6/2009 | Brunner et al. |
| 2013/0243856 A1 | 9/2013 | Dharmadhikari et al. |

OTHER PUBLICATIONS

Chapelle et al., Recherches sur les ènehydrazines, Action de la diméthyl-1,2 hyrazine sur les composés carbonylés: formation de N-méthylpyrroles et de pyrazolines-3 (*). Bullentin De La Societe Chimique de France, 1970 No. 8-9, pp. 3147-. 3155.

Lipkowski et al., "A Novel Pyrrole Synthesis Via Reaction of Ketones With N-Aminoimides", Tretrahedron Letters, 1986, vol. 27, No. 36 pp. 4257-4260.

Katritzky et al., "The Synthesis of some Alkylbenzocarbazoles", J. Hetercyclic Chem., 1988, vol. 25, pp. 671-675.

Fritz et al., "Synthese von Pyrrolen, Pyrazolinen und Pyrazolen über Bis-en-hydrazine", Liebigs Ann. Chem., 1971, vol. 744, pp. 81-87.

Schmidhammer et al., A Simple and Efficient Method for the Preparation of Binaltrorphimine and Derivatives and Determination of their κ Opioid Antagonist Selectivity Helvetica Chimica ACTA, vol. 72, 1989, pp. 675-677.

Portoghese et al., "Binaltorphinmine-Related bivalent Ligands and their κ Opioid Receptor Antagonist", J. Med. Chem., 1988, vol. 31, pp. 836-841.

Portoghese et al., "Only One Pharmacophore is Required for the κ Opioid Antagonist Selectivity of Norbinaltorphimine", J. Med. Chem., 1988, vol. 31, pp. 1344-1347.

Chapelle et al., "Recherches dur les ènehydrazines, Action de la méthylhydrazine sur less cétones: formation de N-méthylphrroles", Bullentin De La Societe Chimique de France, 1971 No. 1 pp. 280-283.

International Search Report and Written Opinion for International Application No. PCT/US2016-023107, dated May 27, 2016, 10 pages.

Filer, "Morphinan Alkaloids Labeled with Tritium: Synthesis and Applications," Journal of Labeled Compounds, and Radiopharmaceuticals, 2013, vol. 56, pp. 639-648.

Portoghese, P.S. et al.: Bimorphinans as highly selective, potent k opioid receptor antagonists. J. Med. Chem., vol. 30, pp. 238-239, 1987.

* cited by examiner

*Primary Examiner* — Charanjit Aulakh
(74) *Attorney, Agent, or Firm* — Morgan, Lewis & Bockius LLP

(57) ABSTRACT

The present invention in various aspects relates to the synthesis of pyrrole-linked bivalent compounds, including but not limited to norBNI, as well as pharmaceutical compositions comprising the same.

16 Claims, 4 Drawing Sheets

FIG. 1

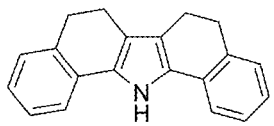

Tamaru, Y.; Harada, T.; Yoshida, Z-I *J. Org. Chem.* 1978, *43*, 3370-3374.

6,7,8,13-Tetrahydro-5*H*-dibenzo[*a,i*]carbazole

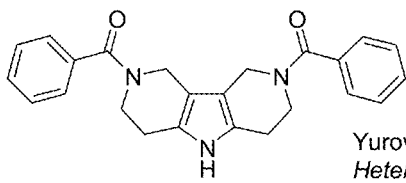

Yurovskaya, M. A.; Alekseyev, R. S. *Chemistry of Heterocyclic Compounds*, 2014, *49*, 1400-1425.

(6-Benzoyl-1,2,4,5,6,7,8,9-octahydro-3,6,9-triaza-fluoren-3-yl)-phenyl-methanone

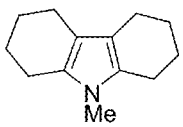

Yurovskaya, M. A.; Alekseyev, R. S. *Chemistry of Heterocyclic Compounds*, 2014, *49*, 1400-1425.

9-Methyl-2,3,4,5,6,7,8,9-octahydro-1*H*-carbazole

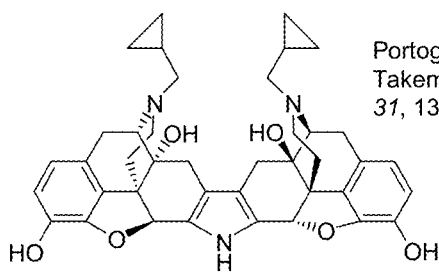

Portoghese, P. S.; Nagase, H.; Takemori, A. E. *J. Med. Chem.* 1988, *31*, 1344-1347.

norBNI enantiomer

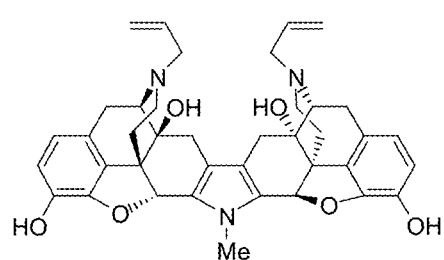

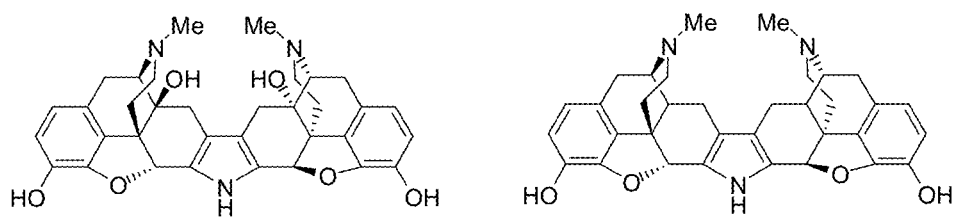

Portoghese, P. S.; Nagase, H.; Lipkowski, A. W.; Larson, D. L.; Takemori, A. E. *J. Med. Chem.* 1988, *31*, 836-841.

METHODS FOR THE CHEMICAL SYNTHESIS OF PYRROLE-LINKED BIVALENT COMPOUNDS, AND COMPOSITIONS THEREOF

FIELD

The present invention in various aspects relates to the synthesis of pyrrole-linked bivalent compounds, including but not limited to norBNI, as well as pharmaceutical compositions comprising the same.

BACKGROUND OF THE INVENTION

Selective κ Opioid Receptor (KOPR) Antagonists, including the compound known as norBNI (nor-binaltorphimine), have been investigated for their therapeutic properties and used as tools in opioid research. norBNI and analogs thereof are considered to act as a bivalent ligand for KOPR, with the pyrrole acting essentially as a spacer.

Current methods for the chemical synthesis of norBNI and related compounds from, for example, naltrexone, proceed in two steps by Piloty synthesis. The first step involves the synthesis of the azine intermediate by reacting naltrexone with hydrazine, followed by change of solvent for conversion of the azine to norBNI. Portoghese P S et al., *Binaltorphimine-Related Bivalent Ligands* and *Their κ Opioid Receptor Antagonist Selectivity*, J. Med. Chem. 31:836-841 (1988). The yield of the reaction is low (e.g., 40-60%), and the process is not sufficiently scalable. Further, the known synthesis may produce reaction by-products with unintended pharmacological activity, or otherwise include potentially toxic impurities that are difficult to remove.

It is an object of the invention to provide improved methods for the chemical synthesis of norBNI and related compounds, as well as compositions of such active agents that are suitable for pharmaceutical use.

BRIEF SUMMARY OF THE INVENTION

In various aspects, the invention provides a process for the chemical synthesis of pyrrole-linked bivalent compounds, such as those of Formula I:

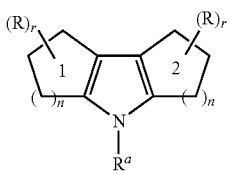

Formula I

In Formula I: $R^a$ is hydrogen or a substituent; each n is an integer independently selected from 0, 1, 2, 3, and 4; each r is an integer ranging from 0 to (2n+4); and each R is a substituent wherein two or more neighboring R groups may optionally form a hydrocarbon or heterocyclic ring system. An exemplary compound of Formula I is nor-binaltorphimine (norBNI), a selective antagonist of the κ Opioid Receptor (KOPR). The processes described herein provide substantial improvements in yield, cost, and scalability, and in some embodiments, avoid the production of toxic impurities and/or reaction by-products that may have undesirable pharmacological activity.

In various embodiments, the reaction takes place as a one-pot synthesis (e.g., without solvent exchange and/or without isolation of an intermediate), thereby improving yield, cost, and simplifying the process. The process is scalable. For example, the process can be conducted at small scale (e.g., with 10 g of starting material such as naltrexone), or at a commercial scale (e.g., 100 kg or more of starting material such as naltrexone).

In various embodiments, the reaction can proceed with about 0.1 to about 10 molar equivalents of hydrazine reactant with respect to naltrexone (or compound of Formula II as described herein). In certain embodiments, the reaction contains less than about 2 molar equivalents of hydrazine reactant with respect to naltrexone (or compound of Formula II), or about 0.5 molar equivalents of hydrazine reactant with respect to naltrexone (or compound of Formula II).

In other embodiments, the reaction takes place with an N-aminoimide reactant, such as tert-butyl (2,5-dioxopyrrolidin-1-yl)carbamate, which can be present in the reaction at from about 0.1 to about 10 molar equivalents (with respect to naltrexone or compound of Formula II).

The reaction is conducted in a solvent, which in various embodiments is a polar solvent, such as a solvent selected from DMF (dimethylformamide), water, and alcohol (e.g., methanol or ethanol).

In some embodiments, the reaction is conducted in the presence of a catalyst. For example, the catalyst can be an organic acid, an inorganic acid, or a combination thereof. In some embodiments, the catalyst comprises methanesulfonic acid ($MeSO_3H$) and/or sulfuric acid.

In some embodiments, the method comprises degassing the reaction mixture. For example, the method may comprise sparging the reaction mixture with an inert gas, which may be argon or nitrogen in some embodiments. These embodiments provide substantial improvements in the impurity profile of the product, generally greater than about 99% AUC by HPLC.

Illustrative embodiments of the invention include the production of norBNI from naltrexone and hydrazine, using DMF as the solvent, and $MeSO_3H$ as a catalyst in a one-pot reaction (e.g., without solvent exchange). Such reactions can involve about 0.5 to about 1 molar equivalents of hydrazine with respect to naltrexone, and from about 3 to about 5 molar equivalents of $MeSO_3H$ with respect to naltrexone.

The process allows simple recovery of the product. For example, in some embodiments, the recovery of norBNI does not comprise chromatography and/or chemical extraction. The recovery of norBNI in some embodiments comprises collecting a precipitant of the reaction product, and converting the product to a pharmaceutically acceptable salt. In various embodiments, the salt is a dichloride salt, or alternatively is a tartrate, citrate, diacetate, sulfate, or phosphate salt, or a mixed salt.

In other aspects, the invention provides a composition prepared by the methods as described herein, such as norBNI compositions, or other compositions based on compounds of Formula I. In various embodiments, the compositions avoid impurities in the prior processes.

In other aspects, the invention provides pharmaceutical compositions comprising a pharmaceutically acceptable salt of norBNI selected from tartrate, citrate, diacetate, sulfate or phosphate, and a pharmaceutically acceptable carrier or excipient.

DESCRIPTION OF THE FIGURES

FIG. 1 shows various compounds of Formula 1 that may be synthesized in accordance with the processes described herein.

DETAILED DESCRIPTION OF THE INVENTION

Figure 2A:
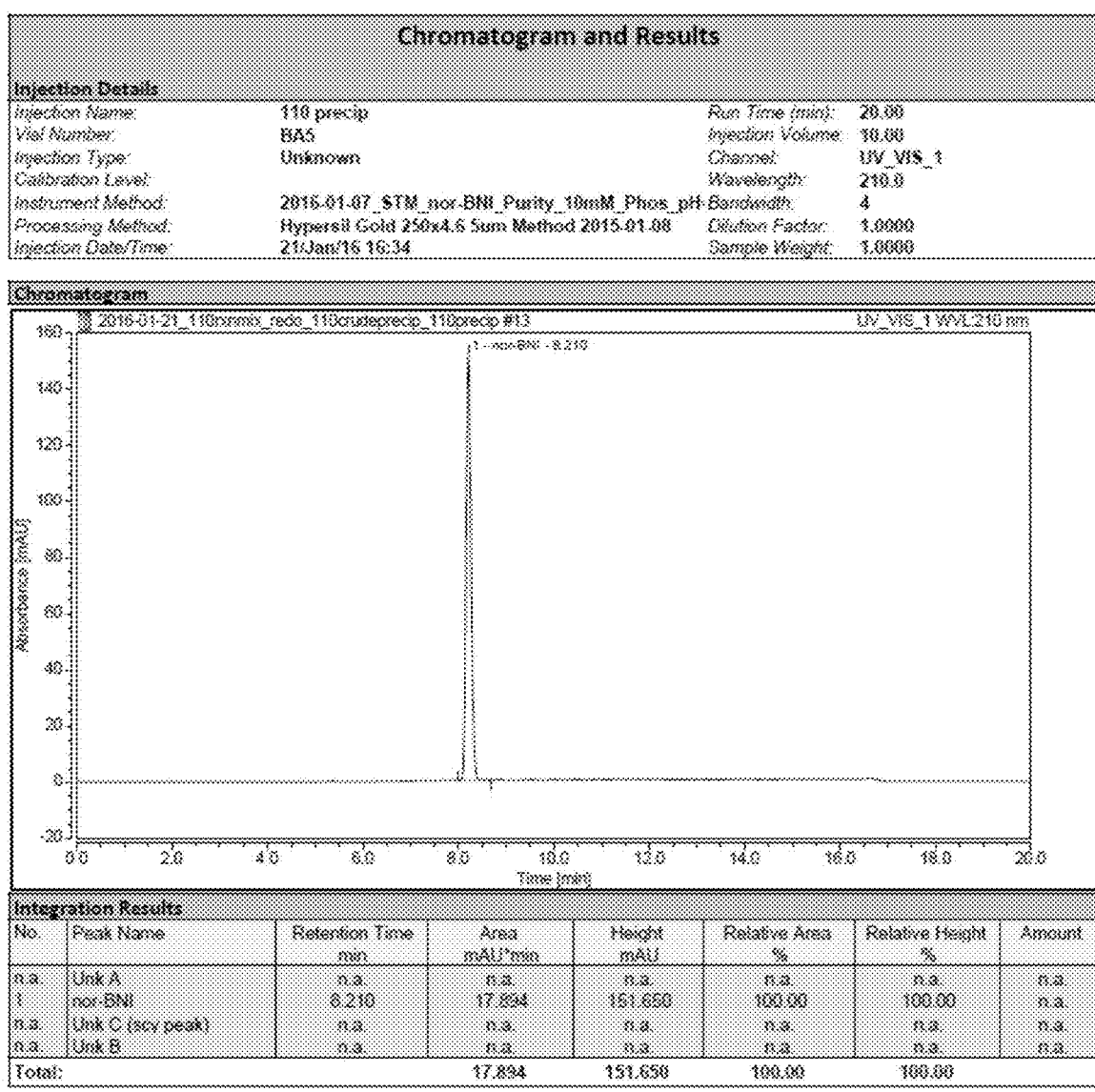
FIG. 2(A-C) are example HPLC spectra for production of norBNI free base, as well as chloride and sulfate salts according to embodiments of the invention. The HPLC spectra show that the products are near 100% pure.

In one aspect, the present invention provides a process for chemical synthesis of a compound having the structure of Formula I or salt thereof:

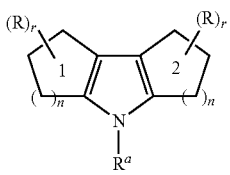

Formula I

In Formula I: $R^a$ is hydrogen or a substituent; each n is an integer independently selected from 0, 1, 2, 3, and 4; each r is an integer ranging from 0 to (2n+4); and each R is a substituent wherein two or more neighboring R groups may optionally form a hydrocarbon or heterocyclic ring system. An exemplary compound of Formula I is nor-binaltorphimine (norBNI). norBNI and related compounds are selective antagonists of the κ Opioid Receptor (KOPR), and are promising therapeutic candidates for Attention Deficit/Hyperactivity Disorder (ADHD). See US 2014/0113924, the entire disclosure of which is hereby incorporated by reference. The present invention provides processes for the chemical synthesis of norBNI and related compounds (e.g., which may be defined in some embodiments as bivalent receptor ligands, linked by a pyrrole). Such processes provide substantial improvements in yield, cost, and scalability, and in some embodiments, avoid the production of toxic impurities and/or reaction by-products that have undesirable pharmacological activity.

Accordingly, in other aspects, the invention provides compounds and compositions prepared by the methods described herein. The invention further provides pharmaceutical compositions of norBNI or related compounds, including pharmaceutically-acceptable salts.

In certain embodiments, the process for synthesizing a compound of Formula I or a salt thereof comprises the step of reacting a compound of Formula II with a hydrazine reactant of Formula III or a salt thereof under reaction conditions sufficient to produce the compound of Formula I. In Formula III, $R^d$ and $R^e$ are independently hydrogen or a substituent, and in Formula II, Z is O, S, or $NR^f$, wherein $R^f$ is hydrogen or a substituent. All other groups are as defined above for Formula I.

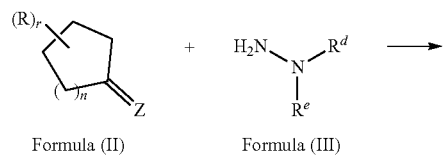

Formula (II)     Formula (III)

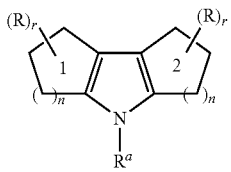

Formula (I)

Alternatively, the process for synthesizing a compound of Formula I or salt thereof comprises the step of reacting an N-aminoimide reactant with a compound of Formula II, under reaction conditions sufficient to produce a compound of Formula I. N-aminoimide reactants include (2,5-dioxopyrrolidin-1-yl)carbamate, including protected derivatives (e.g., tert-butyl (2,5-dioxopyrrolidin-1-yl)carbamate). Alternative N-aminoimide reactants include aminomaleimide or aminoglutarimide, or salts thereof (e.g., hydrochloride salt). In these embodiments, the invention provides yields of about 75% or greater, or about 85% or greater, such as 90% or greater. As disclosed further below, these embodiments may employ methane sulfonic acid as a catalyst.

In some embodiments, the method produces a compound of Formula I(A), where each of $R^{1a}$ to $R^{9a}$ is independently selected from hydrogen or a substituent:

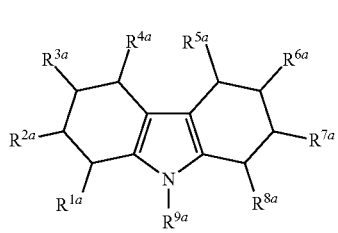

Formula I(A)

In some embodiments, the compound of Formula I(A) is symmetrical, with the 6-membered rings containing identical substituents.

In certain embodiments, the product of the process is a salt of Formula I(B) or a free base of Formula I(C):

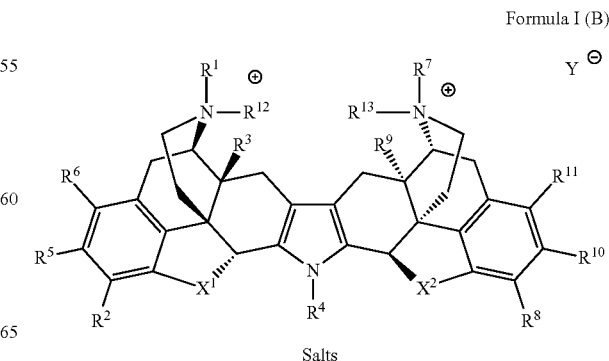

Formula I (B)

Salts

-continued

Formula I (C)

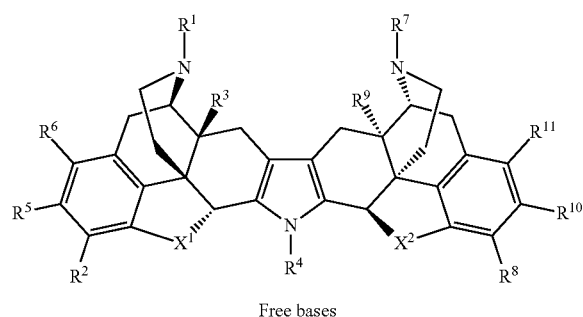

Free bases

In Formulas I(B) and I(C), each of $R^1$-$R^{13}$ or $R^1$-$R^{11}$ is independently hydrogen or a substituent as defined herein; $X^1$ and $X^2$ are independently any heteroatom, such as O, N, S, P, or B. In Formula I(B), Y is a negatively charged counter-ion.

In various embodiments, the method produces nor-binaltorphimine (norBNI) or salt thereof, by reacting naltrexone or salt thereof with hydrazine in a polar solvent. For example, for illustration, the process can take place according to the following scheme, using DMF as an exemplary solvent:

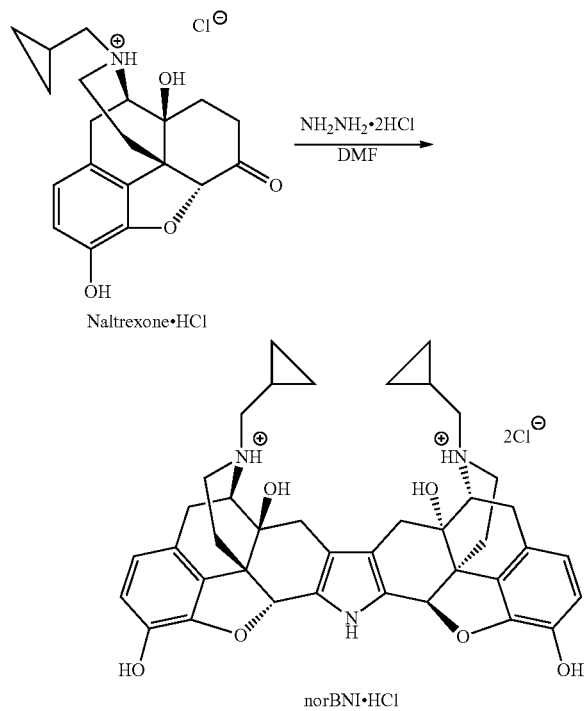

In various embodiments, the reaction takes place as a one-pot synthesis (e.g., without solvent exchange and/or without isolation of an intermediate), thereby improving yield, cost, and simplifying the process. For example, in some embodiments, the process for production of the compound or composition described herein (starting with the compound of Formula II) does not include chromatographic separation of by-products or chemical extraction. In various embodiments, the product of the reaction is at least about 70% norBNI, or is at least about 75% norBNI, or is at least about 80% norBNI, or is at least about 85% norBNI, or is at least about 90% norBNI, or is at least about 95% norBNI, or is at least about 96% norBNI, or is at least about 97% norBNI, or is at least 98% norBNI, or is at least 99% norBNI, or is at least 99.5% norBNI. These yields are substantial improvements over known processes.

In these embodiments, the product of the reaction may contain fewer reaction by-products, such as the corresponding azine. For example, the azine corresponding to norBNI, which has been considered to be an intermediate, can have the following structure (shown as a dichloride salt):

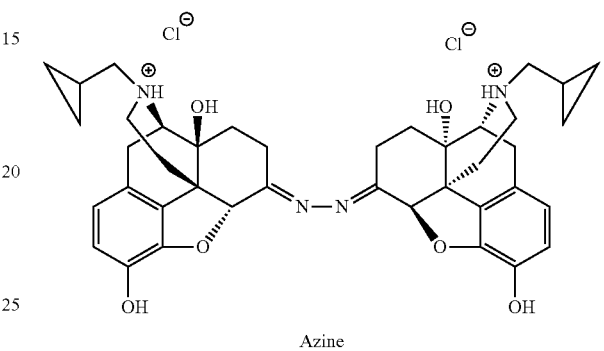

Azine

In various embodiments, the reaction product contains the corresponding azine at less than about 30%, or less than about 25%, or less than about 20%, or less than about 15%, or less than about 10%, or less than about 5%, or less than about 4%, or less than about 3%, or less than about 2%, or less than about 1% of total product, or less than about 0.5% of total product. In some embodiments, the azine is not detectable as a reaction product.

The process of the invention in various embodiments does not require a long reaction time. For example, the reaction generally proceeds for less than about 15 hours, or less than about 12 hours, or less than about 10 hours, or less than about 8 hours, or less than about 6 hours, or less than about 4 hours, or less than about 3 hours, or less than about 2 hours. In various embodiments, the reaction proceeds for 1 to about 5 hours, or for 1 to about 4 hours.

The various features make the process easily scalable. For example, the reaction in various embodiments may be conducted with at least about 10 g of a compound of Formula II (e.g., naltrexone), or at least about 50 g of a compound of Formula II (e.g., naltrexone), or at least about 100 g of a compound of Formula II (e.g., naltrexone), or at least about 500 g of a compound of Formula II (e.g., naltrexone), or at least about 1 kg of a compound of Formula II (e.g., naltrexone), or at least about 20 kg of a compound of Formula II (e.g., naltrexone), or at least about 50 kg of a compound of Formula II (e.g., naltrexone), or at least about 100 kg of a compound of Formula II (e.g., naltrexone), or at least about 200 kg of a compound of Formula II (e.g., naltrexone), or about 500 kg of a compound of Formula II (e.g., naltrexone).

In various embodiments, the method does not rely on high concentrations of hydrazine to drive the reaction, and in such embodiments, the invention may employ higher molar equivalents of the compound of Formula II. For example, the concentration of naltrexone (or related compound of Formula II) in the reaction is about 0.3M or greater, about 0.4M or greater, or about 0.5M or greater. Generally, the concentration of naltrexone or compound of Formula II in the reaction will be from about 0.1M to about 1M (e.g., from 0.4M to 1M or from 0.5M to 1M). In various embodiments, the reaction contains from about 0.1 to about 10 molar equivalents of hydrazine reactant (Formula III) with respect to naltrexone (or compound of Formula II), such as from about 0.2 to about 5 molar equivalents of hydrazine reactant with respect to naltrexone (or compound of Formula II). In certain embodiments, the reaction contains less than about 2 molar equivalents of hydrazine reactant with respect to naltrexone (or compound of Formula II), or about 0.5 molar equivalents of hydrazine reactant with respect to naltrexone (or compound of Formula II).

The reaction is conducted in a solvent, which in various embodiments is organic, inorganic, polar, or nonpolar. Where the solvent is polar, the solvent can be protic or aprotic. In some embodiments, the reaction is performed in an organic solvent, which may be an aprotic organic solvent. In some embodiments, the reaction is performed in a solvent having both high dielectric constant and/or high dipole moment. In some embodiments, the solvent is a polar solvent selected from DMF (dimethylformamide), water, alcohol (e.g., methanol, ethanol, isopropanol, butanol, tert-butanol etc.), acetonitrile, DMSO, or mixtures thereof. In some embodiments, the solvent is DMF. Examples of solvents that can be used in the present invention and their relative polarities are detailed in Table 1:

TABLE 1

Solvents Arranged According To Increasing Polarity

| Solvent | boiling point (° C.) | melting point (° C.) | density (g/mL) | solubility in $H_2O$[1] (g/100 g) | relative polarity[2] |
|---|---|---|---|---|---|
| cyclohexane | 80.7 | 6.6 | 0.779 | 0.005 | 0.006 |
| pentane | 36.1 | −129.7 | 0.626 | 0.0039 | 0.009 |
| hexane | 69 | −95 | 0.655 | 0.0014 | 0.009 |
| heptane | 98 | −90.6 | 0.684 | 0.0003 | 0.012 |
| carbon tetrachloride | 76.7 | −22.4 | 1.594 | 0.08 | 0.052 |
| carbon disulfide | 46.3 | −111.6 | 1.263 | 0.2 | 0.065 |
| p-xylene | 138.3 | 13.3 | 0.861 | 0.02 | 0.074 |
| toluene | 110.6 | −93 | 0.867 | 0.05 | 0.099 |
| benzene | 80.1 | 5.5 | 0.879 | 0.18 | 0.111 |
| ether | 34.6 | −116.3 | 0.713 | 7.5 | 0.117 |
| methyl t-butyl ether (MTBE) | 55.2 | −109 | 0.741 | 4.8 | 0.124 |
| dioxane | 101.1 | 11.8 | 1.033 | M | 0.164 |
| N,N-dimethylaniline | 194.2 | 2.4 | 0.956 | 0.14 | 0.179 |
| chlorobenzene | 132 | −45.6 | 1.106 | 0.05 | 0.188 |
| anisole | 153.7 | −37.5 | 0.996 | 0.10 | 0.198 |
| tetrahydrofuran (THF) | 66 | −108.4 | 0.886 | 30 | 0.207 |
| ethyl acetate | 77 | −83.6 | 0.894 | 8.7 | 0.228 |
| ethyl benzoate | 213 | −34.6 | 1.047 | 0.07 | 0.228 |
| dimethoxyethane (glyme) | 85 | −58 | 0.868 | M | 0.231 |
| diglyme | 162 | −64 | 0.945 | M | 0.244 |
| methyl acetate | 56.9 | −98.1 | 0.933 | 24.4 | 0.253 |
| chloroform | 61.2 | −63.5 | 1.498 | 0.8 | 0.259 |
| 1,1-dichloroethane | 57.3 | −97.0 | 1.176 | 0.5 | 0.269 |
| di-n-butyl phthalate | 340 | −35 | 1.049 | 0.0011 | 0.272 |
| dimethylphthalate | 283.8 | 1 | 1.190 | 0.43 | 0.309 |
| methylene chloride | 39.8 | −96.7 | 1.326 | 1.32 | 0.309 |
| 1,2-dichloroethane | 83.5 | −35.4 | 1.235 | 0.87 | 0.327 |
| benzonitrile | 205 | −13 | 0.996 | 0.2 | 0.333 |
| acetone | 56.2 | −94.3 | 0.786 | M | 0.355 |
| dimethylformamide (DMF) | 153 | −61 | 0.944 | M | 0.386 |
| t-butyl alcohol | 82.2 | 25.5 | 0.786 | M | 0.389 |
| dimethylsulfoxide (DMSO) | 189 | 18.4 | 1.092 | M | 0.444 |
| acetonitrile | 81.6 | −46 | 0.786 | M | 0.460 |
| 3-pentanol | 115.3 | −8 | 0.821 | 5.1 | 0.463 |
| 2-pentanol | 119.0 | −50 | 0.810 | 4.5 | 0.488 |
| 2-butanol | 99.5 | −114.7 | 0.808 | 18.1 | 0.506 |

TABLE 1-continued

Solvents Arranged According To Increasing Polarity

| Solvent | boiling point (° C.) | melting point (° C.) | density (g/mL) | solubility in $H_2O$[1] (g/100 g) | relative polarity[2] |
|---|---|---|---|---|---|
| cyclohexanol | 161.1 | 25.2 | 0.962 | 4.2 | 0.509 |
| 1-octanol | 194.4 | −15 | 0.827 | 0.096 | 0.537 |
| 2-propanol | 82.4 | −88.5 | 0.785 | M | 0.546 |
| 1-heptanol | 176.4 | −35 | 0.819 | 0.17 | 0.549 |
| i-butanol | 107.9 | −108.2 | 0.803 | 8.5 | 0.552 |
| 1-hexanol | 158 | −46.7 | 0.814 | 0.59 | 0.559 |
| 1-pentanol | 138.0 | −78.2 | 0.814 | 2.2 | 0.568 |
| ethyl acetoacetate | 180.4 | −80 | 1.028 | 2.9 | 0.577 |
| 1-butanol | 117.6 | −89.5 | 0.81 | 7.7 | 0.586 |
| benzyl alcohol | 205.4 | −15.3 | 1.042 | 3.5 | 0.608 |
| 1-propanol | 97 | −126 | 0.803 | M | 0.617 |
| acetic acid | 118 | 16.6 | 1.049 | M | 0.648 |
| ethanol | 78.5 | −114.1 | 0.789 | M | 0.654 |
| diethylene glycol | 245 | −10 | 1.118 | M | 0.713 |
| methanol | 64.6 | −98 | 0.791 | M | 0.762 |
| ethylene glycol | 197 | −13 | 1.115 | M | 0.790 |
| glycerin | 290 | 17.8 | 1.261 | M | 0.812 |
| water, heavy | 101.3 | 4 | 1.107 | M | 0.991 |
| water | 100.00 | 0.00 | 0.998 | M | 1.000 |

Legend:
[1]M = miscible with water.
[2]The values for relative polarity are normalized from measurements of solvent shifts of absorption spectra and were extracted from Christian Reichardt, *Solvents and Solvent Effects in Organic Chemistry*, Wiley-VCH Publishers, 3rd ed., 2003.

In some embodiments, the reaction is conducted in the presence of a catalyst. For example, the catalyst can be an organic acid, an inorganic acid, or a combination thereof. In some preferred embodiments, the catalyst comprises a Lewis acid alone or in combination with other acids.

In various embodiments, the catalyst comprises organic sulfonic acid such as alkylsulfonic acid, arylsulfonic acid, and cycloalkylsulfonic acid. Exemplary organic sulfonic acids include methanesulfonic acid and ethanesulfonic acid. In some embodiments, the catalyst comprises a mineral acid. Exemplary mineral acids include, but are not limited to, hydrochloric acid, nitric acid, sulfuric acid, phosphoric acid, and combinations thereof.

In some preferred embodiments, the catalyst comprises methanesulfonic acid ($MeSO_3H$) and/or sulfuric acid.

In various embodiments, the acid catalyst in the reaction is from about 0.5 to about 5 molar equivalents with respect to the compound of Formula II. In some embodiments using less than 2 or less than 1 molar equivalent of hydrazine reactant (e.g. with respect to the compound of Formula II), the reaction includes from about 3 to about 5 (e.g., about 4) molar equivalents of $MeSO_3H$ (with respect to the compound of Formula II).

The reaction conditions in the process of the present invention are selected appropriately depending on the identity of the compound of Formula II as the starting material, the kind of hydrazine reactant of Formula III (or kind of N-aminoimide reactant in alternative embodiments), or the kind of catalysts or solvents used. The molar ratio of hydrazine reactant to the compound of Formula II in some embodiments is in the range of about 0.5 to about 1, but in consideration of catalyst to be used in combination with the hydrazine reactant, it may be desirable to maintain the ratio of the hydrazine reactant at about 0.5, while varying the ratio of the catalyst in the range of about 0.5 to about 5 (with respect to the compound of Formula II).

In some embodiments, the method comprises degassing the reaction mixture, such as by sparging the reaction mixture with an inert gas, which may be argon, nitrogen, or helium in some embodiments. These embodiments provide substantial improvements in the impurity profile of the product, generally greater than about 99% AUC by HPLC, or greater than about 99.5% in some embodiments, or greater than about 99.8% in some embodiments, or greater than 99.9% in some embodiments. In these embodiments, chromatographic separation and/or chemical extraction is generally unnecessary in the preparation of the product.

While the reaction conditions can vary, in some embodiments, the reaction is maintained within the temperature of from about 50° C. to about 110° C., and optionally from about 95° C. to about 105° C.

Illustrative embodiments include the production of a compound of Formula I from a compound of Formula II, with the hydrazine reactant of Formula III, using DMF as the solvent, and MeSO$_3$H as a catalyst. In some embodiments, the process produces norBNI from naltrexone and hydrazine in a one-pot synthesis. Such reactions can involve about 0.5 to about 1 molar equivalent of hydrazine with respect to naltrexone, and from about 3 to about 5 molar equivalents of MeSO$_3$H with respect to naltrexone.

The process allows simple recovery of the product. While the recovery of the product (e.g., norBNI) can comprise purifying the product from one or more secondary reaction products or reactants, such steps are not be necessary in some embodiments. For example, in some embodiments, the recovery of norBNI does not comprise chromatography and/or extraction. The recovery of norBNI in some embodiments comprises collecting a precipitant of the reaction product (e.g., by filtration), and converting the product (having a yield as already described) to a pharmaceutically acceptable salt. In various embodiments, the salt is a dichloride salt, or alternatively is a tartrate, citrate, diacetate, sulfate, or phosphate salt, or a mixed salt.

In formation of norBNI salts, in some embodiments the reaction is monitored to avoid the addition of excess acid. The reaction may be monitored for an abrupt change in the trend between increasing volume of acid added, verses conductance or pH of the reaction mixture, indicating the equivalence point of the reaction. The salt formation reaction may be monitored with a conductivity meter, pH meter, ion-sensitive electrode, or other suitable means.

The process as described is useful for producing various compounds of Formula I, from compounds of Formula II:

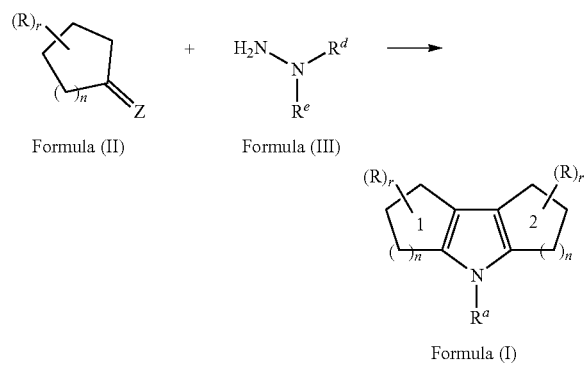

Formula (II)    Formula (III)

Formula (I)

In certain embodiments, the reactant of Formula II is a cycloalkanone where Z is O. Exemplary cycloalkanones include, but are not limited to substituted and unsubstituted cyclobutanones, substituted and unsubstituted cyclopentanones, substituted and unsubstituted cyclohexanones, substituted and unsubstituted cycloheptanones, and substituted and unsubstituted cyclooctanones.

Two or more adjacent or distal R groups of the compound of Formula II may optionally form a hydrocarbon or heterocyclic ring system. In some embodiments, two neighboring R groups form a ring system independently selected from phenyl, thienyl, furanyl, pyrimidinyl, oxazoyl, thiazolyl, pyridyl, naphthyl, quinolinyl, indolyl, benzothiophenyl, benzofuranyl, pyrrolyl, imidazolyl, pyrazole, triazolyl, isoxazolyl, pyridazinyl, pyrazinyl, pyrimidinyl, oxadiazolyl, benzimidazolyl, and triazinyl, each of which may contain substituents. In some embodiments, two or more neighboring R groups form a heterocyclic system containing one or more heteroatoms selected from the group consisting of as oxygen, sulfur, nitrogen, and combinations thereof.

In some embodiments, $R^d$ and $R^e$ of the hydrazine reactant of the Formula III are both hydrogen, or in some embodiments, one or both of $R^d$ and $R^e$ is a lower alkyl (e.g., methyl or ethyl) or alkoxy, hydroxyl, a halogen, or an amine. In some embodiments, the hydrazine reactant comprises hydrazine sulfate, hydrazine hydrochloride, hydrazine dihydrochloride, hydrazine monohydrochloride, hydrazine monohydrobromide, hydrazine acetate, hydrazine sulfate, and mixtures thereof. $R^d$ or $R^e$ have the same identity as $R^a$ of Formula I.

Substituents as identified for compounds of Formulas I-III, may be independently selected from any suitable substituent. Generally, suitable substituents include, but are not limited to acyl, acyloxy, alkyl, heteroalkyl, alkenyl, heteroalkenyl, alkynyl, heteroalkynyl, alkoxy, alkoxycarbonyl, cycloalkyl, heterocycloalkyl, aryl, arylalkyl, heteroaryl, heteroarylalkyl, hydroxy, halo, cyano, trifluoromethyl, trifluoromethoxy, nitro, and trimethylsilanyl. Exemplary substituents include those independently selected from ethers, esters, sulfides, disulfides, sulfonyl, sulfinyl, sulfonamidyl, sulfonate, sulfoxyl, phosphate esters, phosphines, borate esters, halogens, carbonyl, carboxylate, carbamate, amines, imides, and quanidines. For example, exemplary substituents include Cl, F, Br, —OR$^b$, —SR$^b$, —OC(O)—R$^b$, —N(R$^b$)$_2$, —C(O)R$^b$, —C(O)OR$^b$, —OC(O)N(R$^b$)$_2$, —C(O)N(R$^b$)$_2$, —N(R$^b$)C(O)OR$^b$, —N(R$^b$)C(O)R$^b$, —N(R$^b$)C(O)N(R$^b$)$_2$, N(R$^b$)C(NR$^b$)N(R$^b$)$_2$, —N(R$^b$)S(O)$_2$R$^b$, —S(O)OR$^b$, —S(O)$_2$OR$^b$, —S(O)N(R$^b$)$_2$, —S(O)$_2$N(R$^b$)$_2$, or PO$_3$(R$^b$)$_2$ where each R$^b$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

Alkyl substituents may be straight or branched, and may be substituted or unsubstituted (e.g., haloalkyl). In some embodiments, the alkyl group may have from 1 to 12 carbon atoms, e.g. 1 carbon atom, 2 carbon atoms, 3 carbon atoms, 4 carbon atoms etc., up to and including about 12 carbon atoms. Exemplary alkyl groups include methyl, ethyl, propyl, isopropyl, n-butyl, iso-butyl, sec-butyl isobutyl, tertiary butyl, pentyl, isopentyl, neopentyl, hexyl, septyl, octyl, nonyl and decyl. The alkyl substituent may be attached to the rest of the molecule by a single bond.

Alkenyl substituents may be straight or branched, and may be substituted or unsubstituted. In some embodiments, the alkenyl group may contain from 2 carbon atoms to about 12 carbon atoms, e.g., the alkenyl group may consist of 2 carbon atoms, 3 carbon atoms, 4 carbon atoms etc., up to and including about 12 carbon atoms. The alkenyl substituent may be attached to the rest of the molecule by a single bond or by a double bond.

Alkynyl substituents may be straight or branched, and may be substituted or unsubstituted. In some embodiments, the alkynyl group contains from 2 to about 12 carbon atoms (e.g., 2, 3, or 4 carbon atoms). The alkynyl may be attached to the rest of the molecule by a single bond, for example, ethynyl, propynyl, butynyl, pentynyl and hexynyl.

Cycloalkyl substituents may be monocyclic or polycyclic substituents, which may be saturated, or partially unsaturated, and may be substituted or unsubstituted. In some embodiments, cycloalkyl substituents are selected from those having from 3 to 12 ring atoms. Illustrative examples of cycloalkyl substituents include, but are not limited to cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

Alkoxy substituents are defined by the group —O-alkyl. In some embodiments, the alkoxy group contains from 1 to 12 carbon atoms of a straight, branched, cyclic configuration and combinations thereof attached to the parent structure through an oxygen. Exemplary alkoxy substituents include, but are not limited to, methoxy, ethoxy, propoxy, isopropoxy, cyclopropyloxy and cyclohexyloxy. In some embodiments, the alkoxy is a lower alkoxy (containing one to six carbon atoms). The alkoxy substituent is optionally substituted.

Alkoxycarbonyl substituents include substituents of the formula (alkoxy)(C=O)-attached through the carbonyl carbon. In some embodiments, the alkoxycarbonyl group contain from 1 to 12 carbon atoms, e.g., C(1-12)-alkoxycarbonyl group. In some embodiments, the alkoxycarbonyl is a lower alkoxycarbonyl (containing 1 to 6 carbon atoms). The alkoxycarbonyl may be substituted or unsubstituted.

Acyl substituents include substituents of the formula Rx-C(O)—, where Rx is alkyl, heteroalkyl, alkenyl, alkynyl, cycloalkyl, heterocycloalkyl, aryl, arylalkyl, heteroaryl, and heteroarylalkyl, each as described herein.

Acyloxy substituents include those of the formula Rx(C=O)O—, where Rx is alkyl, heteroalkyl, alkenyl, alkynyl, cycloalkyl, heterocycloalkyl, aryl, arylalkyl, heteroaryl, heteroarylalkyl, each as described herein.

Amino or "amine" substituents include those of the formula —N(R$^b$)$_2$, where Rb is hydrogen, alkyl, (halo)alkyl, alkenyl, alkynyl, carbocyclyl, carbocyclylalkyl, aryl, aralkyl, heterocycloalkyl, heterocycloalkylalkyl, heteroaryl heteroarylalkyl, or other substituent described herein. When —N(R$_b$)$^2$ has two R$_b$ substituents other than hydrogen, they can be combined with the nitrogen atom to form a 4-, 5-, 6- or 7-membered ring. For example, —N(R$_b$)$^2$ is intended to include, for example, pyrrolidinyl and morpholinyl.

Amide or "amido" substituents include those of the formula —C(O)N(R$^y$)$_2$ or —NHC(O)R$^y$, where R$^y$ is selected from the group consisting of hydrogen, alkyl, alkenyl, alkynyl, carbocyclyl, carbocyclylalkyl, cycloalkyl, aryl, heteroaryl, or other substituent described herein. The R$^y$ of —N(R$^y$)$_2$ of the amide may optionally be taken together with the nitrogen to which it is attached to form a 4-, 5-, 6- or 7-membered ring.

In some embodiments, a substituent is aromatic, meaning that the substituent is an unsaturated, cyclic and planar hydrocarbon group with a delocalized conjugated π system having 4n+2 π electrons, where n is an integer having a value of 0, 1, 2, 3, and so on. In some embodiments, the aromatic group is an "aryl", which refers to an aromatic radical with six to ten ring atoms. That is, an aryl substituent has at least one ring having a conjugated pi electron system which is carbocyclic. Aryl includes monocyclic or fused-ring polycyclic groups. Aryl may include substituents as described herein, for example, "aralkyl" or "arylalkyl". Aryl includes carbocyclic and heterocyclic ring systems.

An "ester" as used herein refers to a chemical radical of formula —COOR$_z$, where R$_z$ includes, but is not limited to, alkyl, alkenyl, alkynyl, alkyl, alkenyl, alkynyl, cycloalkyl, cycloalkenyl, heterocyclyl, aryl, heteroaryl, aralkyl, and heteraralkyl, or other substituent described herein.

In some embodiments, the substituent is a halogen (e.g., fluoro, chloro, bromo or iodo). Thus, substituents include haloalkyl, haloalkenyl, haloalkynyl and haloalkoxy.

In some embodiments, a substituent is sulfanyl, which refers to substituents that include —S-(optionally substituted alkyl), —S-(optionally substituted aryl), —S-(optionally substituted heteroaryl) and —S-(optionally substituted heterocycloalkyl). In some embodiments, at least one substituent is a sulfinyl, which refers to substituents that include —S(O)—H, —S(O)-(optionally substituted alkyl), —S(O)-(optionally substituted amino), —S(O)-(optionally substituted aryl), S(O)-(optionally substituted heteroaryl) and —S(O)-(optionally substituted heterocycloalkyl). In some embodiments, at least one substituent is sulfonyl, which refers to substituents that include —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl). In some embodiments, at least one substituent is sulfonamidyl, which refers to a —S(=O)$_2$—NR$_2$ radical. In some embodiments, at least one substituent is sulfoxyl, which refers to a —S(=O)$_2$OH substituent. In some embodiments, at least one substituent is a sulfonate, which refers to a —S(=O)$_2$—OR radical.

Heteroalkyl, heteroalkenyl, and heteroalkynyl substituents include optionally substituted alkyl, alkenyl and alkynyl radicals and which have one or more skeletal chain atoms selected from an atom other than carbon, e.g., oxygen, nitrogen, sulfur, phosphorus or combinations thereof.

In some embodiments, the compound of Formula I is a salt of Formula I(B) or free base of Formula I(C):

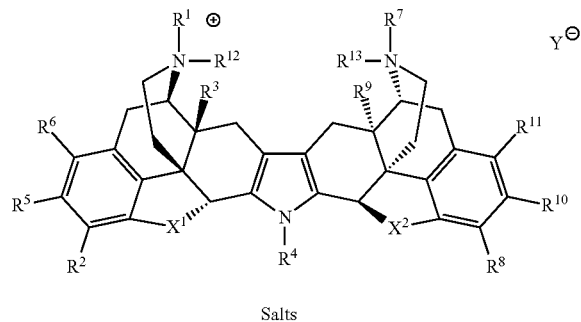

Formula 1 (B)

Salts

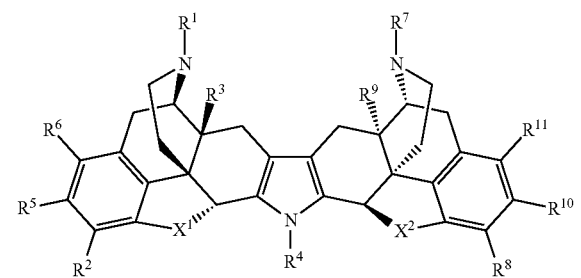

Formula 1 (C)

Free bases where each of $X^1$ and $X^2$ is O, N, or S, and each of $R^1$ to $R^{11}$ or $R^1$ to $R^{13}$ is independently selected from hydrogen, hydroxide, amino, halogen. C1-6-alkyl, C1-6-alkenyl, C1-C6 alkynyl, C1-C6 alkyl ketone, phenyl ketone, C1-C6 alkyl imine, phenyl imine, C1-C6 alkyl amide, benzyl amide, benzamide, C1-C6 alkyl ester, benzoyl, phenyl ester, carboxylate, C1-C6 alkyl carbonate, phenyl carbonate, carbamate, C1-C6 monoalkyl carbamate, C1-C6 dialkyl carbamate, phenyl carbamate, diphenyl carbamate, guanidine, C1-C6 alkyl ether, phenyl, benzyl, benzyl ether, phenyl ether, trifluoromethyl, trfluoromethoxy, trifluroacetate, sulfonic acid, C1-C6 alkyl sulfonate ester, trifluromethanesulfonate, toluenesulfonate, benzene sulfonate, phenyl sulfoxide, C1-C6 alkyl sulfoxide, nitro, cyano, isonitrile, C1-C6 epoxide, C1-C6 monoalkyl amine, C1-C6 dialkyl amine, diphenyl amine, phosphate, C1-C6 alkyl phosphate, C1-C6 dialkyl phosphate, phosphine, C1-C6 monoalkyl phosphine, C1-C6 dialkyl phosphine, phenyl phosphine, diphenylphosphine, C1-C6 monoalkyl phenyl phosphine, boronic acid, C1-C6 dialkyl boronic ester, diphenyl boronic ester, borate, C1-C6 dialkyl borate, and diphenyl borate. Y is a negatively charged counter-ion, either a dianion or two monoanions.

Appropriate reagents of Formula II and III can be easily selected according to the identity of required substituents.

For example, Formula II may have the structure of Formula II (A):

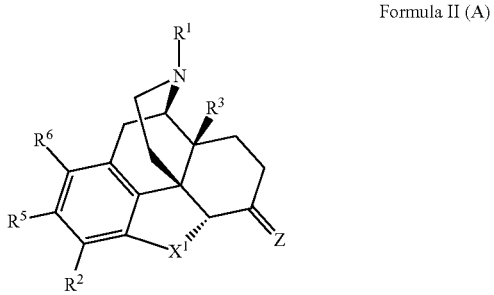

Formula II (A)

where each of $R^1$ to $R^3$, and $R^5$ and $R^6$ has the same meaning as described for the compounds of Formulas I(B) and I(C); and $Z^1$ is O, S, or $NR^f$, wherein $R^f$ is hydrogen or a substituent. Reaction of the compound of Formula II(A) with the hydrazine reagent (having substituent R4 in Formula I(B) or (C)), produces a bivalent compound of Formula I(B) or (C).

Exemplary compounds of Formula I, which may be synthesized in accordance with the invention, include those shown in FIG. 1.

The invention includes methods of making and compositions of various isomers and stereoisomers (including enantiomers, diasteriomers, and racemic mixtures) of nor-BNI and related compounds. The term "(±)" is used to designate a racemic mixture where appropriate. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral reagents, or resolved using conventional techniques.

In other aspects, the invention provides a composition prepared by the method as described herein, such as norBNI compositions, or other compositions based on compounds of Formula I. In various embodiments, the compositions avoid impurities in the prior process, such as, for example, DMSO and/or corresponding azine compounds. While DMSO has been used to convert an azine intermediate to norBNI, the present invention provides a direct (one-pot) synthesis from naltrexone to norBNI (for example) and which does not require solvent exchange to DMSO.

Thus, the invention provides norBNI compositions that are highly pure, without reaction impurities, such as compositions that are at least 99% norBNI or salt thereof, with respect to norBNI and reaction impurities as 100%, or at least 99.5% norBNI or salt thereof. The compositions may be scaled batches of active ingredient, and thus contain at least 100 g of norBNI or salt thereof, or at least 500 g of norBNI or salt thereof, or at least 1 kg of norBNI or salt thereof. In still other embodiments, the norBNI composition is a pharmaceutical composition comprising a pharmaceutically effective amount of norBNI or salt thereof.

In other aspects, the invention provides pharmaceutical compositions comprising a pharmaceutically acceptable salt of norBNI selected from tartrate, citrate, diacetate, sulfate or phosphate, and a pharmaceutically acceptable carrier.

Pharmaceutical compositions can take any suitable form depending on the desired administration route (e.g., oral), including tablets, capsules, aerosols, biodegradable matrices for sublingual or buccal administration, topical composition or transdermal patch, suppositories, or injectable solutions. Various pharmaceutical carriers and excipients may be used according to standard practice in the industry. In some embodiments, the composition does not contain more than 1% reaction impurities with respect to the amount of norBNI, or does not contain more than 0.5% reaction impurities with respect to the amount of norBNI.

EXAMPLES

Example 1: Preparation of Nor-Binaltorphimine (Nor-BNI) from Naltrexone Hydrochloride The preparation of nor-binaltorphimine dihydrochloride (norBNI.2HCl) from naltrexone hydrochloride using hydrazine dihydrochloride has been described (*J. Med. Chem.* 1988, 31, 836-841). The process is a two-step procedure via an intermediate azine.

Scheme 1

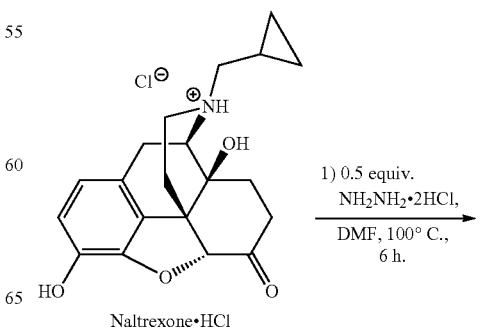

Naltrexone•HCl 1) 0.5 equiv. NH$_2$NH$_2$•2HCl, DMF, 100° C., 6 h.

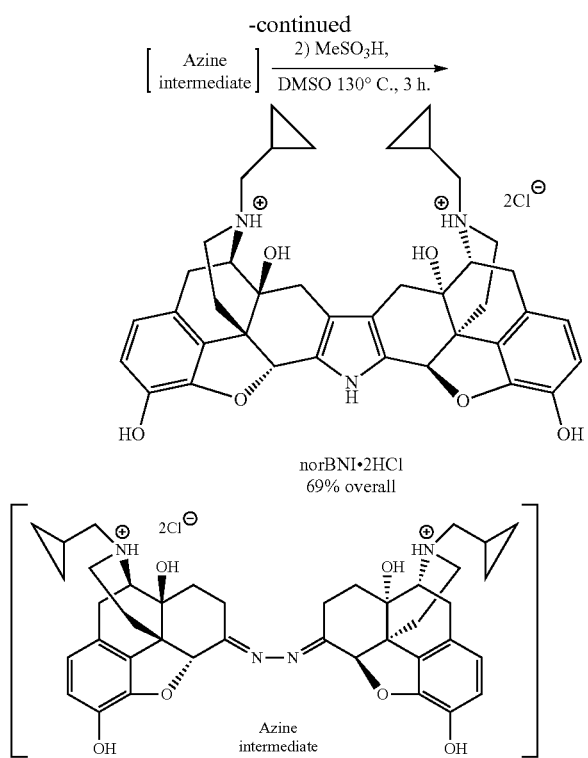

In the following example, norBNI is produced directly from naltrexone and hydrazine, without solvent exchange, according to Scheme 2:

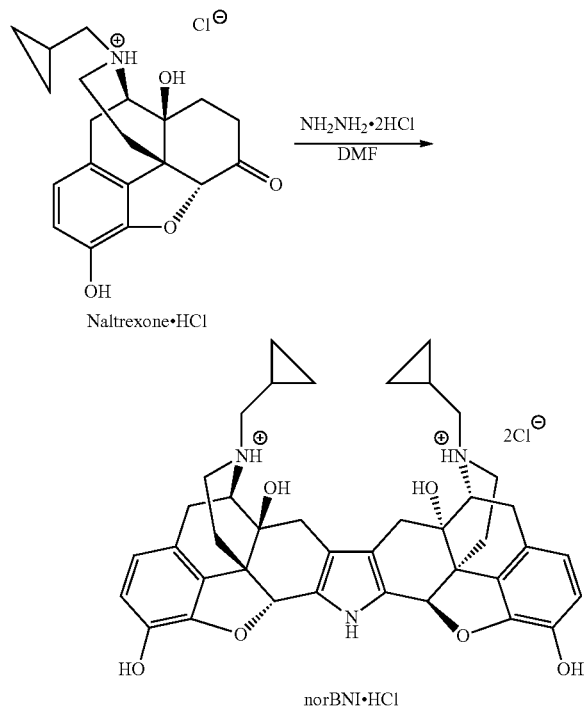

To a previously dried 250-mL, two-necked round bottomed flask equipped with a stirring bar and flushed with argon is added in the following order, 200 mL of DMF (anhydrous, Sigma Aldrich), 50 g (132.32 mmol) of naltrexone.HCl (Siegfried), 6.95 g (66.16 mmol) of hydrazine.2HCl (Sigma Aldrich) and 35.1 mL (529.28 mmol) of methanesulfonic acid (Sigma Aldrich). On addition of methanesulfonic acid an exotherm is noted and the bulk of the reagents are seen to dissolve (full dissolution of the reagents is seen to take up to an hour). After stirring for 10 minutes a reflux condenser is attached and the reaction mixture is heated to 105° C. The reaction is monitored by $^1$H NMR analysis of small aliquots of the reaction mixture every hour. When the reaction is complete, typically after 3 hours, the flask is taken off the heat and allowed to cool for 15 minutes. To the reaction mixture is then added 200 mL of water followed by 160 mL of aqueous ammonium hydroxide (29%, Fisher Scientific) to basify the reaction mixture. The resulting precipitate is collected by filtration and washed with a further 200 mL of water and allowed to dry to give crude norBNI contaminated with DMF as a beige solid. To remove DMF, the crude product is dissolved in a minimum quantity of methanol (400 mL) and to this solution water (600 mL) is slowly added, with stirring, to re-precipitate the product. The suspension is then stirred at room temperature for 3 hours, before the precipitate is collected by filtration, washed with a further volume of water (200 mL) and allowed to dry, to give norBNI (free base) as a beige/off white amorphous solid (42 g, 96% yield, 96.8% purity). The identity of the compound was confirmed by HRMS analysis and $^1$H and $^{13}$C NMR, which were in agreement with previously published data. Compound purity was determined by UHPLC.

This scheme eliminates the second step (e.g., the use of DMSO) and provides a significant improvement in yield, for example from 69% to around 96%.

Example 2: Reaction Parameters

Increasing molar equivalents of hydrazine reactant, for example, hydrazine hydrochloride, from 0.5 to 2 or more molar equivalents per molar equivalent of naltrexone hydrochloride, an example of the compound of Formula (II), significantly increases the yield of the reaction product of Formula (I), e.g., norBNI.2HCl, from 9% to at least 90% (see Table 2). This increase in the yield of the product, e.g., norBNI.2HCl, is observed without isolating any intermediates or intermediary compounds, e.g. azine in Scheme 1, and/or without change of the reaction solvent. Similarly, addition of at least one catalyst, e.g. methanesulfonic acid, can significantly increase the yield of norBNI.2HCl formed from 9% to at least 90%. This increase in yield of the reaction product did not require a concomitant increase in the number of molar equivalents of the hydrazine reactant used and did not require isolation of an intermediary azine product or change of the reaction solvent. Using 4 molar equivalents of MeSO$_3$H resulted in a norBNI yield of 87%, with only 0.5 molar equivalents of hydrazine.

TABLE 2

Conversion of the azine into norBNI•2HCl in the presence of a catalyst

| Entry | Scale/mmol of naltrexone[1] | Equiv. of hydrazine•HCl | Equiv. of MeSO₃H | Temperature (° C.) | Azine Yield (%) | norBNI Yield (%)[2,3] |
|---|---|---|---|---|---|---|
| 1 | 1.6 (0.6 g) | 0.5 | 0 | 100 | 80 | 9 |
| 2 | 1.6 | 1 | 0 | 100 | 67 | 5 |
| 3 | 1.6 | 2 | 0 | 100 | 27 | 26 |
| 4 | 1.6 | 4 | 0 | 100 | 0 | 74 |
| 5 | 1.6 | 4 | 1 | 110 | 0 | 90 |
| 6 | 1.6 | 0.5 | 1 | 109 | 30 | 60 |
| 7 | 1.6 | 1 | 1 | 110 | 0 | 89 |
| 8 | 1.6 | 0.5 | 4 | 110 | 0 | 87 |

[1]Naltrexone used purchased from A K Scientific.
[2]For entries 1-11, product yields diminished by presence of 5-10% water in the naltrexone from A K Scientific.
[3]Isolated as the free base after basic work-up.

Methanol was also shown to be an acceptable solvent, preferably including 1 equivalent of methanesulfonic acid, and providing yields of around 80% at a 1.6 mmol scale. The reaction was also successfully carried out in water, but proceeds at a slower rate. Preferably, the solvent is polar, such that reaction components sufficiently dissolve.

The reaction was also successfully carried out with sulfonic acid as the catalyst, which also required a longer reaction time.

A range of temperatures were examined. While the reaction is not dependent on a particular temperature range, some decomposition can occur above 110° C., as evident from $^1$H NMR (possibly caused by degradation of the DMF). However, the effect on the yield was not significant.

The order and rate of addition of the reaction components showed no significant effect on the outcome of the reaction.

The process described herein is commercially scalable. It advantageously simplifies synthesis of the pyrrole-containing compound by eliminating isolation of intermediate compounds and/or also eliminating any solvent changing steps. Thus, the process can advantageously be carried out as a one-pot, one-solvent process. Moreover, the process leads to improvements in yields of the reaction product, and work-up procedure (e.g. eliminates use of expensive extraction techniques and chromatography). In an exemplary work-up procedure, the product precipitate (basified with aqueous ammonium hydroxide) is collected by filtration, dissolved in organic solvent such as methanol, re-precipitated with water, and the precipitate collected again by filtration. The free base can be converted to the desired salt, e.g., the dichloride salt by addition to HCl-ethyl acetate solution.

Six salt forms were made: dichloride, diacetate, tartrate, citrate, phosphate, and sulfate. Salts are made by addition of a slight excess of the corresponding acid to a saturated solution of norBNI free base in ethyl acetate. The precipitated salt is collected and washed with a further portion of ethyl acetate before being allowed to dry. Conversions are quantified and the salts are isolated often as white/cream amorphous solid. Salts derived from strong mineral acids such as the hydrochloride and sulfate salts can be stirred in EtOAc overnight to remove excess acid residues, which appear to render the salts hygroscopic. Traces of DMF can also be removed by this method. The compounds appear pure by $^1$H NMR and HPLC analysis.

TABLE 3

Commercially Scalable Process

| Entry | Scale/mmol of naltrexone[1] | Equiv. of hydrazine•HCl | Equiv. of MeSO₃H | Temperature (° C.) | Azine Yield (%) | norBNI Yield (%)[2,3] |
|---|---|---|---|---|---|---|
| 1 | 16 (6 g) | 1 | 1.5 | r.t. to 105 | 0 | 86 |
| 2 | 32 (12 g) | 0.5 | 4 | r.t. to 105 | 0 | 91 |
| 3 | 64 (24 g) | 0.5 | 4 | r.t. to 105 | 0 | 87 |
| 4 | 132 (50 g) | 0.5 | 4 | r.t. to 105 | 0 | 96 |

[1]Naltrexone used purchased from A K Scientific except for entry 4 (Siegfried).
[2]For entries 1-3, product yields diminished by presence of 5-10% water in the naltrexone from A K Scientific.
[3]Isolated as the free base after basic work-up.

TABLE 4

A Study Of Effect Of The Reaction Concentration

| Entry | Scale/mmol (naltrexone) | Concentration/ M[1] | NorBNI Yield |
|---|---|---|---|
| 1[2] | 1.6 | 0.13 | 87 |
| 2[2] | 1.6 | 0.26 | 89 |
| 3[3] | 16 | 0.16 | 86 |
| 4[4] | 32 | 0.29 | 91 |
| 5[4] | 64 | 0.55 | 87 |
| 6[4] | 132 | 0.56 | 96 |

[1]Molar concentration is calculated taking into account both the volume of DMF and MeSO₃H.
[2]Hydrazine HCl (0.5 eq.), MeSO₃H (4 eq.), 110° C., azine 0%;
[3]Hydrazine HCl (1 eq.), MeSO₃H (1.5 eq.), r.t. to 105° C., azine 0%; and
[4]MeSO₃H (1 eq.), 3.25 h, r.t. to 105° C., azine 0%.

Table 4 above shows reaction yield is concentration invariant. Varying naltrexone from 0.16 M-0.56 M has little, if any, impact on the yield or rate of the reaction. At a 50 g scale the reaction was conducted at a 0.56 M concentration in a DMF (200 mL)/methanesulfonic acid (35 mL) solution.

Example 3: Production of Nor-BNI Products of High Purity

The production of norBNI products of high purity was achieved using the method given above in Example 1 but with the following modifications.

The reaction solvent was sparged with an inert gas (nitrogen or argon) for 30 minutes at ≥200 mL/min for a 100 g scale reaction to remove dissolved oxygen. The reaction mixture was then sparged with inert gas for at least a further 80 minutes.

Absolute ethanol was used in place of methanol for the reaction work up and in the salt formation process.

During the salt formation step, the acid was added as a 1 M ethanolic solution. The reaction mixture was monitored to ensure that the addition of excess acid was minimized. This was accomplished with the use of a conductivity probe, where an abrupt change in the trend between increasing volume of acid added, verses conductance of the reaction mixture, indicated the equivalence point of the reaction more precisely.

Figure 2B:
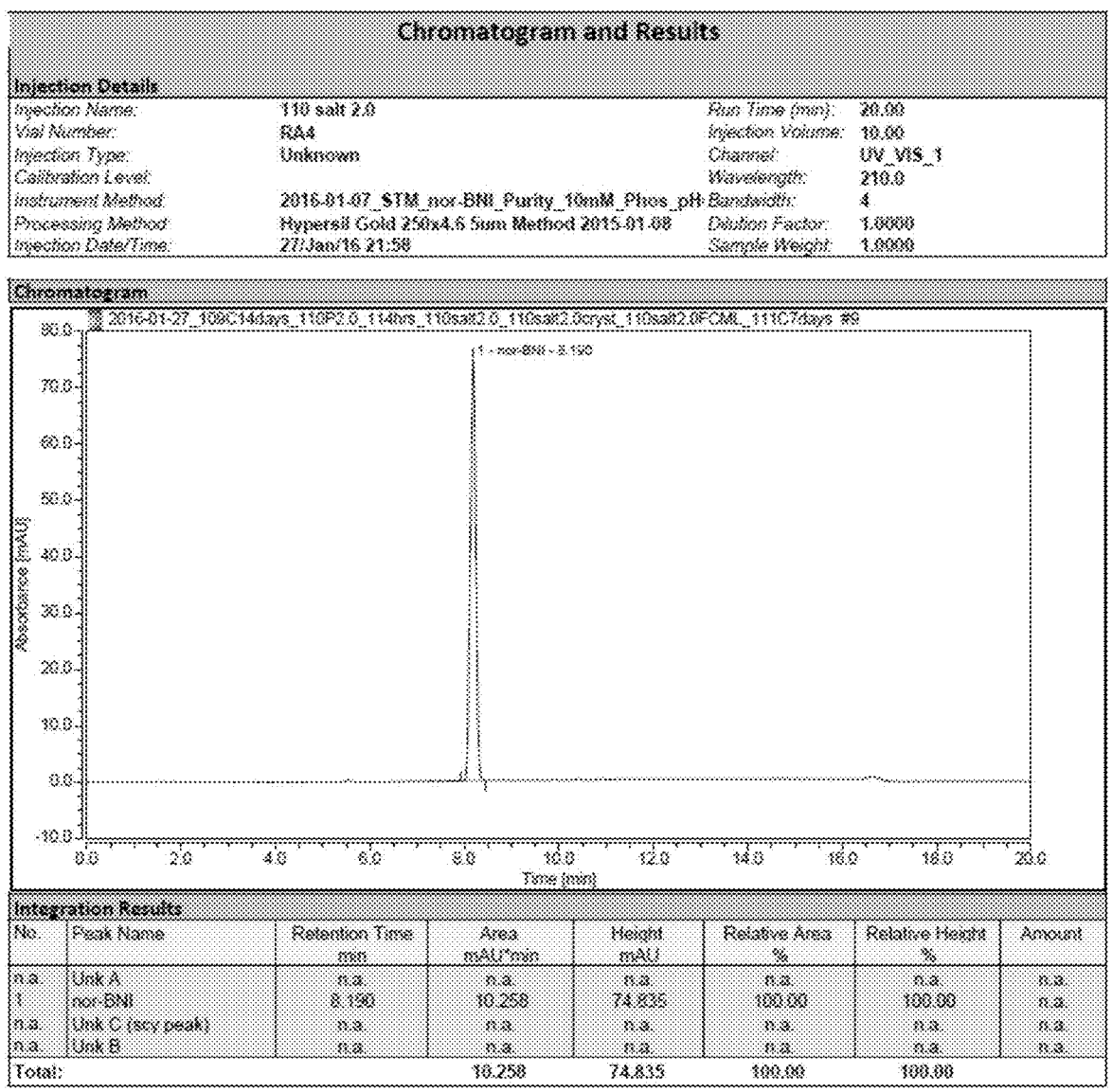
Figure 2C:
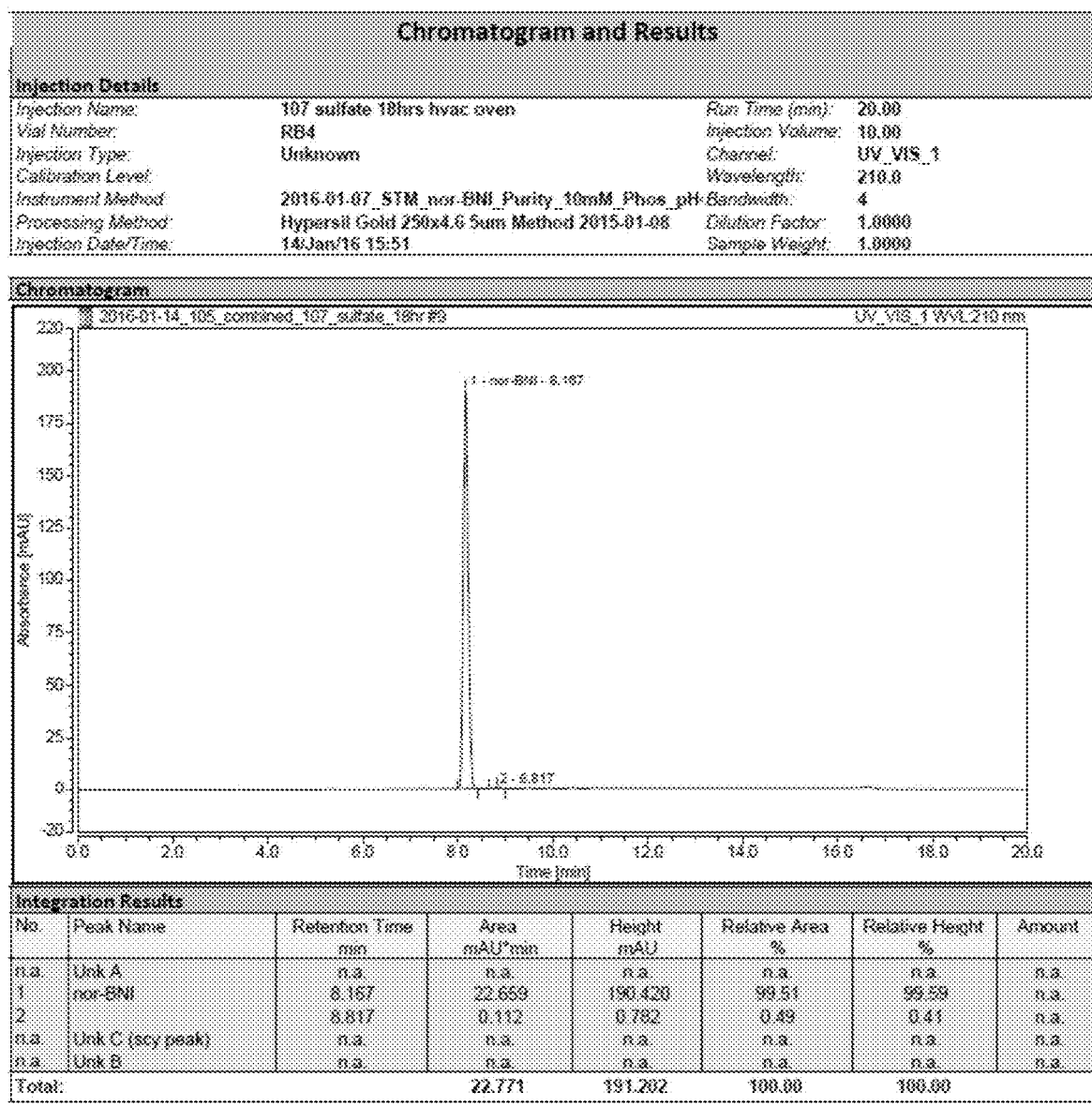

FIG. 2(A-C) are example HPLC spectra of high purity norBNI free base, chloride salt and sulfate salt obtained from this process. The HPLC spectra show that the products are near 100% pure.

Example 4: Alternative Scheme for Production of Nor-BNI from Naltrexone Hydrochloride The following scheme provides an experimental procedure for the synthesis of NorBNI free-base from naltrexone using tert-butyl (2,5-dioxopyrrolidin-1-yl) carbamate as a substitute for hydrazine (Scheme 3).

Scheme 3

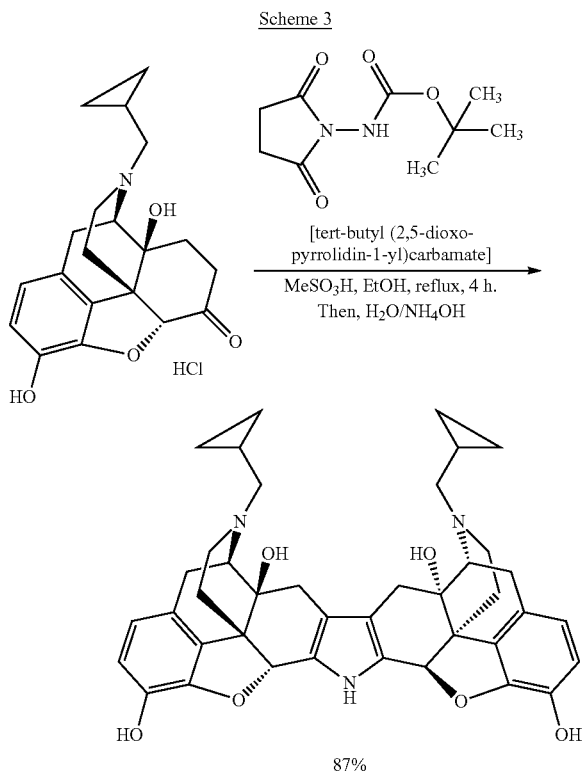

To a 2-necked round bottomed flask equipped with a reflux condenser and a stirrer bar was added absolute ethanol (11 mL), under an atmosphere of inert gas (argon or nitrogen). The absolute ethanol was sparged for at least 10 minutes with inert gas before Naltrexone.HCl (1.09 g, 2.65 mmol) and tert-butyl (2,5-dioxopyrrolidin-1-yl) carbamate (0.65 g, 3.00 mmol) were added with stirring. Upon full dissolution of the reagents, methane sulfonic acid (0.78 mL, 12.00 mmol) was added via syringe in one portion and the reaction was heated to 70° C. The reaction was then left for 4 h, during which time the reaction mixture was seen to turn black. The reaction mixture was then removed from the heat and allowed to cool to r.t. An aliquot of the reaction material analyzed by $^1$H NMR indicated 100% conversion of the starting material. The cooled reaction mixture was then diluted with 22 mL of deionized water, and excess ammonium hydroxide (Aqueous 29%, 99 mL) was added to basify the mixture and precipitate the free base. The light beige material was then collected by filtration through a Buchner funnel and washed with a further 30 mL of water. The product was then dried in a vacuum oven at r.t. for 48 h to give 0.76 g (87%) of NorBNI free base. The identity of the compound was confirmed by $^1$H NMR analysis.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined.

Unless specifically set forth herein, the terms "a", "an" and "the" are not limited to one element but instead should be read as meaning "at least one".

The invention claimed is:

1. A process for a chemical synthesis of norBNI or a related pyrrole-linked bivalent compound having the structure of Formula I(C):

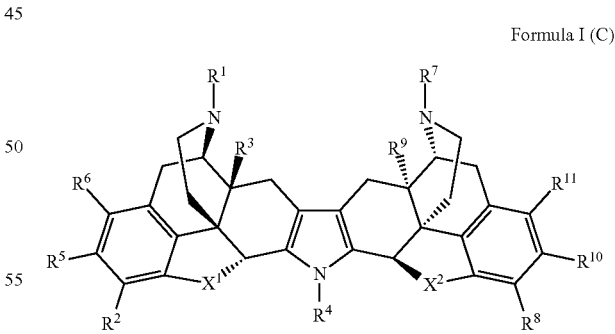

Formula I (C)

or a salt thereof, wherein:
each of $X^1$ and $X^2$ is O, N, or S, and each of $R^1$ to $R^{11}$ is independently selected from hydrogen or a substituent the process comprising reacting naltrexone or related compound for producing the bivalent compound of Formula I(C)
with a hydrazine reagent in a reaction solvent under reaction conditions sufficient to produce the compound of Formula I(C) or salt thereof without exchanging the reaction solvent, and wherein the reaction conditions comprise the presense of an alkylsulfonic acid as a catalyst.

2. The process of claim 1, wherein the compound of Formula I(C) is nor-binaltorphimine (norBNI).

3. The process of claim 1, wherein the hydrazine reagent is a compound of the formula $H_2N-N(R)_2$, wherein each R is H or an independently selected substituent.

4. The process of claim 3, wherein the process produces nor-binaltorphimine (norBNI) or salt thereof, by reacting naltrexone, or salt thereof, with hydrazine in a polar solvent.

5. The process of any one of claims 1, wherein the reaction takes place as a one-pot synthesis.

6. The process of any one of claims 1, wherein the process does not include chromatographic separation of by-products or chemical extraction.

7. The process of claim 1, wherein the concentration of the compound of naltrexone or related compound in the reaction is about 0.3M or greater.

8. The process of claim 1, wherein the concentration of the naltrexone or related compound in the reaction is from about 0.1M to about 1M.

9. The process of any one of claims 1, wherein the reaction contains from about 0.1 to about 10 molar equivalents of hydrazine reactant with respect to the naltrexone or related compound.

10. The process of claim 9, wherein the reaction contains from about 0.2 to about 5 molar equivalents of hydrazine reactant with respect to the naltrexone or related compound.

11. The process of claim 10, wherein the reaction contains less than about 2 molar equivalents of hydrazine reactant with respect to the naltrexone or related compound.

12. The process of claim 11, wherein the reaction contains about 0.5 molar equivalents of hydrazine reactant with respect to the naltrexone or related compound.

13. The process of any one of claims 1, wherein the reaction solvent is polar.

14. The process of claim 13, wherein the solvent is selected from DMF (dimethylformamide), water, methanol, ethanol, or mixtures thereof.

15. The process of claim 1, wherein at least one of 1e to $R^1$ is selected from hydroxide, amino, and halogen.

16. The process of claim 1, wherein the naltrexone or related compound has the structure of Formula II(A):

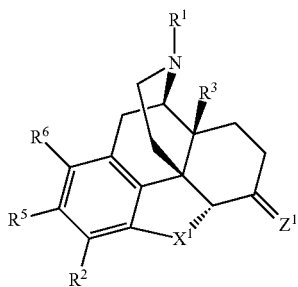

Formula II (A)

where each of $R^1$ or $R^3$, and $R^5$ and $R^6$ has the same meaning as described for the compounds of Formula I(C); and $Z^1$ is O, S, or $NR^f$, wherein $R^f$ is hydrogen or a substituent.

* * * * *